(12) United States Patent
Cooper

(10) Patent No.: US 9,072,689 B2
(45) Date of Patent: Jul. 7, 2015

(54) UNIVERSAL POTENT HEALING TONIC

(71) Applicant: Nathaniel Cooper, Roanoke Rapids, NC (US)

(72) Inventor: Nathaniel Cooper, Roanoke Rapids, NC (US)

( * ) Notice: Subject to any disclaimer, the term of this patent is extended or adjusted under 35 U.S.C. 154(b) by 21 days.

(21) Appl. No.: 13/948,460

(22) Filed: Jul. 23, 2013

(65) Prior Publication Data

US 2014/0271933 A1    Sep. 18, 2014

Related U.S. Application Data

(60) Provisional application No. 61/790,107, filed on Mar. 15, 2013.

(51) Int. Cl.
| | |
|---|---|
| *A61K 33/00* | (2006.01) |
| *A61K 9/00* | (2006.01) |
| *A61K 31/7004* | (2006.01) |
| *A61K 35/644* | (2015.01) |
| *A61K 36/88* | (2006.01) |
| *A23L 1/00* | (2006.01) |

(52) U.S. Cl.
CPC ............. *A61K 33/00* (2013.01); *A61K 35/644* (2013.01); *A61K 36/88* (2013.01); *A23L 1/00* (2013.01); *A61K 31/7004* (2013.01); *A61K 9/0095* (2013.01)

(58) Field of Classification Search
CPC ....... A61K 9/0095; A61K 9/08; A61K 31/70; A61K 33/00; A61K 35/644; A61K 31/7004; A61K 36/88; A23L 1/00
USPC ...................................... 424/717, 43, 44, 439
See application file for complete search history.

(56) References Cited

U.S. PATENT DOCUMENTS

| | | | |
|---|---|---|---|
| 2007/0003613 A1* | 1/2007 | Christy et al. ................ | 424/451 |
| 2011/0288180 A1* | 11/2011 | Korzenik et al. ............. | 514/723 |

OTHER PUBLICATIONS

Mark Sircus Ac., OMD, "Cancer & Sodium Bicarbonate", 2008, Reprint from Regenerative Nutrition, pp. 1-6, [online], International Medical Veritas Association [retrieved on Oct. 6, 2014] Retrieved from the Internet: <URL: http://www.regenerativenutrition.com/printer.asp?id=490.*
Bill Henderson, Cancer Free, Your Guide to Gentle, Non-Toxic Healing, 2004, (publisher unavailable).*
Vernon Johnston, 2008, 'Protocol—My Dance with Cancer' [online], [retrieved Oct. 6, 2014] Retrieved from the Internet: <URL: http://phkillscancer.com/protocol.*

* cited by examiner

*Primary Examiner* — Jane C Oswecki

(57) ABSTRACT

The present invention relates to a method of consuming a universal potent healing tonic. When consumed according to the method, of a host of medical ailments can be abated including cancer, arthritis, and insomnia.

6 Claims, No Drawings

UNIVERSAL POTENT HEALING TONIC

This invention claims benefit and priority to U.S. Provisional Application No. 61/790,107 filed Mar. 15, 2013 under 35 U.S.C. 119.

BACKGROUND

Field of Invention

The present invention relates to a method of consuming a universal potent healing tonic. When consumed according to the method, of a host of medical ailments can be abated including cancer, arthritis, and insomnia.

Home remedies have been used for hundreds of years to alleviate the many ailments of the human body. Sometimes the best solution can be found right in your kitchen. With the elevated, and sometimes unattainable, cost of traditional health care, many people are turning to home remedies for relief. Moreover, many people prefer to use natural products to synthetic pharmaceuticals traditionally offered by physicians.

Since ancient time natural sugars such as honey, molasses, and maple syrup have been cited as a remedy for a host of ailments. Either alone, or in combination, these products have been linked to curing cancer, heart disease, arthritis, bladder infections, cholesterol, toothaches, colds, upset stomach, gas, influenza, skin infections, indigestions, enhancement of immune system, fatigue, halitosis, assist in weight loss, as well as others. Sodium bicarbonate, otherwise commonly known as baking soda, is similarly extolled for its healing properties.

Mainstream science has confirmed that tumor cells can be killed by increasing the pH in their environment. (Dr. Robert Gillies; Wayne State University School of Medicine: "Acidity generated by the tumor microenvironment drives local invasion": Veronica Estrella, Tingan Chen, Mark Lloyd et al. Cancer Research, Published OnlineFirst Jan. 3, 2012; doi: 10.1158/008-5472. CAN-12-2796.) Grants have been given to universities and research institutions to study the effects of pH, including raising pH through sodium bicarbonate, on cancers and arthritis. Still, others believe that raising pH through the use of sodium bicarbonate can eradicate cancer due to the theory that cancer is caused by yeast infection, and the bicarbonate/honey or molasses or syrup combination works to eradicate yeast levels. (Dr. Tullio Simoncini, author of "Cancer is a Fungus").

In combination, sodium bicarbonate and honey, molasses, or maple syrup (hereinafter "natural sugars") have been touted as a cure for many ailments including arthritis, cancer, indigestion, insomnia and many others. Methods and regimens for consuming this combination, however, is something of a mystery. A review of anecdotes and home remedy literature shows a large disparity in recommendations for creating a potent tonic that is safe and effective.

For example the author Bill Henderson in his book "Cancer Free, Your Guide to Gentle, Non-Toxic Healing" uses three parts grade three maple syrup with one part sodium bicarbonate, heating the mixture "for a couple of minutes" on the stove and consuming after the baking soda "foams up." He stores the mixture in the fridge, and consumes one teaspoon of the concoction per day. Another author, Mark Sircus, author of "Sodium Bicarbonate—Rich Man's Poor Man's Cancer Treatment," uses a 7-8 day regimen of molasses with sodium bicarbonate to eradicate cancers.

On another website, one man recounts his battle against prostate cancer that had spread to his bone with the consumption of molasses and baking soda. (see http://phkillscancer.com/protocol). He used one-teaspoon molasses mixed with one-teaspoon baking soda in one cup of water. He took the solution twice a day for 3 days. Then changed his dosage to 2 teaspoons molasses with 2 teaspoons of baking soda in 1 cup of water twice a day for 6 days. On his next body scan, there was no evidence of bone or prostate cancer.

In fact, arguably the largest manufacturer of baking soda gives a regimen for consumption to alleviate indigestion and upset stomach. Arm & Hammer recommends ½ teaspoon in 4 ounces of water every 2 hours as directed by a physician. Not to exceed 7 and ½ teaspoons per 24 hours.

To treat arthritis, physicians like Dr. Parhatsthid Nabadalung from Thailand recommend taking sodium bicarbonate when the urinary pH is below 5.6. Treatment for arthritis, in one person's opinion, is one teaspoon of sodium bicarbonate in 8 ounces of water twice daily.

The average consumer is apt to be confused by the multitude of ingredient combinations, amounts to be used, and frequency of use offered by the present literature. The present method seeks to overcome these hurdles by providing and easy to use system that has resulted in the alleviation of cancer, arthritis, insomnia, and other ailments in the inventor.

Moreover, the measurement of the correct amounts of the universal potent healing tonic can be viewed as cumbersome. A commercial, user-friendly product could be available to assist the user in consuming the appropriate amount of tonic and is described herein as part of the present invention.

BRIEF SUMMARY OF THE INVENTION

According to one aspect of the invention, the method of consuming the universal potent healing tonic consists of a regimen of consuming sodium bicarbonate and molasses in water over the course of approximately 45 days.

According to another aspect of the present invention, sodium bicarbonate is mixed with approximately 6 ounces of boiling water, then molasses is immediately added and the mixture is stirred for approximately 30 seconds. The water/bicarbonate mixture is cooled to lukewarm temperature with ice cubes, and the mixture is consumed.

According to one aspect of the present invention, the method includes consumption of a multivitamin daily, one hour before breakfast.

According to yet another aspect of the present invention, the tonic is prepared and consumed twice daily. The tonic is consumed once before breakfast and one after the final evening meal. This daily rate of consumption is maintained for 15 days (days 1-15).

According to yet another aspect of the present invention, the tonic is then prepared and consumed every other evening for 15 more days (days 16 through 30).

According to another aspect of the present invention, the tonic is then prepared and consumed once per day in the evening meal for 15 additional days (days 31-45).

According to another aspect of the present invention, if symptoms return, repeat the dosage from days 16-30, i.e. consume the tonic every other day in the evening.

According to yet another aspect of the invention, the method should be carried out in conjunction with the consumption of at least three 8 oz. glasses of water per day and not exceeding 16, 8 oz. glasses of water.

According to yet another aspect of the invention, a laxative may be taken while performing the method to avoid or alleviate any constipation.

According to yet another aspect of the invention, daily sugar intake should be reduced to not more than approximately 200 grams.

According to one aspect of the present invention, the method should be performed in conjunction with a healthy diet including fruits and vegetables where possible.

According to another aspect of the invention, to assist the user in performing the method, a kit containing 8 ounces of water in a microwave or heat-able material, as well as a pouch containing the appropriate amount of sodium bicarbonate and the appropriate amount of molasses could be packaged and purchased for use by the consumer.

According to yet another aspect of the invention, separate pouches of sodium bicarbonate and molasses in conjunction with a heat-able container containing 8 ounces of water could be packaged for use by a consumer.

According to one aspect of the invention, a container having markings as to the appropriate amount of sodium bicarbonate, molasses and water could be packaged for use by a consumer.

According to yet another aspect of the invention, a container having markings as to the appropriate amount of water as well as a pouch, either separate or together, with the appropriate amount of sodium bicarbonate and molasses could be packaged and provided for use by a consumer.

DETAILED DESCRIPTION

The invention described in detail herein generally relates to a system for producing and consuming a universal potent healing tonic.

For the purposes of the present invention the term "natural sugars" means all naturally derived sugars including: honey, molasses, and maple syrup.

A full course of using this healing tonic consists of 45 days. During this time, the user will be taking a multivitamin, such as GERITOL® as in the preferred embodiment, before breakfast. As is apparent to those in the art, other multivitamins can be used. Additionally, the user will consume at least three 8 oz. glasses of water per day, and not exceeding sixteen 8 oz. glasses of water. The user's diet should be considered healthy and include 5 servings per day of fruits and vegetables where possible. A laxative may be taken by the user to avoid or alleviate constipation while executing the course.

Consumption of the healing tonic occurs either before breakfast or in the evening, after the final meal of the day. Where the healing tonic is consumed twice daily, during the first 15 days, consumption occurs both before breakfast and in the evening. Where the tonic is consumed once per day or every other day, consumption may occur either before breakfast or in the evening, after the final meal. In the preferred embodiment, the healing tonic is consumed in the evening, after the final meal for the second and third fifteen days. The tonic is made by preparing 8 ounces of boiling water in one container. In another container, place approximately one tablespoon of sodium bicarbonate, and one teaspoon of GRANDMA'S MOLASSES®. As is apparent, other types of molasses may be substituted. Moreover, other natural sugars may be substituted without departing from the scope of the invention. Next, approximately 6 ounces of boiling water is poured into the container with sodium bicarbonate and molasses, and the mixture is gently stirred for approximately 30 seconds or until the contents are in solution.

Alternatively, 6 ounces of boiling water may be mixed with one tablespoon of sodium bicarbonate and the molasses is added immediately thereafter. The mixture is then gently stirred for approximately 30 seconds.

The mixture is then cooled to lukewarm temperature, approximately 90-100° Fahrenheit. This can be accomplished with the addition of ice (approximately two standard ice cubes). Once the mixture is lukewarm, it is consumed.

The mixture is prepared and consumed twice daily, in the morning before breakfast, and in the evening after the last meal, for fifteen consecutive days (days 1-15). Then, the mixture is prepared and consumed every other day, in the evening, for the next fifteen days (days 16-30). Next, the mixture is prepared and consumed once per day, in the evening, for fifteen days (days 31-45). If symptoms recur, the user goes back to the regimen started on day 16. Namely, the mixture is prepared and consumed every other day for 15 days, followed by once a day consumption for 15 days.

Additionally, the mixture may be purchased by the consumer as a kit as is part of the present invention. This kit would include a sealed container of 6 ounces of water. The container is capable of being heated to the boiling temperature of water without degradation. The kit also includes packets of one tablespoon of sodium bicarbonate, and one teaspoon of natural sugars. The packets may be singular (i.e., only sodium bicarbonate), or may have the capability of housing both ingredients without mixing.

Moreover, another embodiment of the kit consisting of a container with markings as to the appropriate amount of water to boil as well as a packets of one tablespoon of sodium bicarbonate, and one teaspoon of natural sugars. The packets may be singular (i.e., only sodium bicarbonate), or may have the capability of housing both ingredients without mixing.

While the invention has been shown and described herein with reference to particular embodiments, it is to be understood that the various additions, substitutions, or modifications of form, structure, arrangement, proportions, materials, and components and otherwise, used in the practice and which are particularly adapted to specific environments and operative requirements, may be made to the described embodiments without departing from the spirit and scope of the present invention. Accordingly, it should be understood that the embodiments disclosed herein are merely illustrative of the principles of the invention. Various other modifications may be made by those skilled in the art, which will embody the principles of the invention and fall within the spirit and the scope thereof.

I claim:

1. A method for consuming a universal potent healing tonic comprising:

a sealed container of approximately 6 ounces of water, said container capable of being heated to approximately 212 degrees Fahrenheit without degradation in the container;

a packet containing approximately 0.5 ounces of sodium bicarbonate and a second packet containing approximately 0.1667 ounces of natural sugar, wherein said packet and second packet may be in one packet containing separate compartments for said 0.5 ounces of sodium bicarbonate and said 0.1667 ounces of natural sugar;

heating the said sealed container with water to approximately 212 degrees Fahrenheit, distributing said packets into said sealed container, mixing said sodium bicarbonate and said natural sugar into solution; and consuming said universal potent healing tonic when it cools to a lukewarm temperature, between approximately 90-100 degrees Fahrenheit, wherein;

the universal potent healing tonic is prepared and consumed once in the morning before a first meal and again in the evening after a last meal for a period of fifteen consecutive days;

after said first period fifteen days the tonic is prepared and consumed once every other day in the evening for a second period of fifteen days; and after said second period of fifteen days the tonic is prepared and consumed once each evening after the last meal for a third period of fifteen days.

2. The method of claim 1, wherein the natural sugar is GRANDMAS MOLASSES®.

3. The method of claim 1, wherein the natural sugar is honey, molasses, or agave syrup.

4. The method of claim 1, wherein if symptoms recur, the universal potent healing tonic is prepared and consumed once every other day in the evening for fifteen days;

after said fifteen days the tonic is prepared and consumed once each evening after the last meal for another set of fifteen days.

5. The method of claim 1, wherein the amount of sodium bicarbonate is 0.25 ounces.

6. The method of claim 1, wherein the user consumes multivitamin, once daily before the first meal.

* * * * *